United States Patent
Gray et al.

(10) Patent No.: US 9,120,737 B2
(45) Date of Patent: Sep. 1, 2015

(54) PROCESS AND SYSTEM FOR THE SEPARATION OF SOLID CARBOXYLIC ACID FINES

(75) Inventors: Julian Stuart Gray, London (GB); Michael William Winter, London (GB)

(73) Assignee: Davy Process Technology Limited, London (GB)

( * ) Notice: Subject to any disclaimer, the term of this patent is extended or adjusted under 35 U.S.C. 154(b) by 68 days.

(21) Appl. No.: 13/702,483

(22) PCT Filed: Jun. 22, 2011

(86) PCT No.: PCT/GB2011/051172
§ 371 (c)(1), (2), (4) Date: Mar. 18, 2013

(87) PCT Pub. No.: WO2012/001390
PCT Pub. Date: Jan. 5, 2012

(65) Prior Publication Data
US 2013/0211134 A1 Aug. 15, 2013

(30) Foreign Application Priority Data

Jun. 30, 2010 (GB) .................................. 1011008.8

(51) Int. Cl.
*C07C 51/47* (2006.01)
*B01D 21/00* (2006.01)

(52) U.S. Cl.
CPC .............. *C07C 51/47* (2013.01); *B01D 21/003* (2013.01)

(58) Field of Classification Search
CPC ........ C07C 51/47; C07C 63/24; C07C 63/26; B01D 21/003

USPC ............................ 422/261, 269, 272; 562/485
See application file for complete search history.

(56) References Cited

U.S. PATENT DOCUMENTS
2002/0003117 A1  1/2002  Ohkoshi et al.

FOREIGN PATENT DOCUMENTS
EP    1669343 A1    6/2006
WO    9730963 A1    8/1997

OTHER PUBLICATIONS

Svarovsky (Solid-Liquid Separation (Fourth Edition), 2001, SN 978-0-7506-4568-3, p. 1-554, http://www.sciencedirect.com/science/book/9780750645683).*

* cited by examiner

*Primary Examiner* — Jafar Parsa
*Assistant Examiner* — Amy C Bonaparte
(74) *Attorney, Agent, or Firm* — Armstrong Teasdale LLP

(57) ABSTRACT

In a process for the separation of solid carboxylic acid fines from mother liquor that includes such fines, the mother liquor is fed to a settlement drum at above atmospheric pressure. The mother liquor having a lower concentration of carboxylic fines than that fed to the settlement drum is then removed, wherein the mother liquor removal occurs at a point above the point at which the mother liquor containing fines is fed to the settlement drum. In a system for performing the separation process, a settlement drum has an inlet for mother liquor with carboxylic acid fines and an outlet for mother liquor having a lower concentration of carboxylic acid fines content than that of the mother liquor introduced via the inlet. The settlement drum is configured to operate at above atmospheric pressure and the outlet is located at a point in the settlement drum above the inlet.

10 Claims, 1 Drawing Sheet

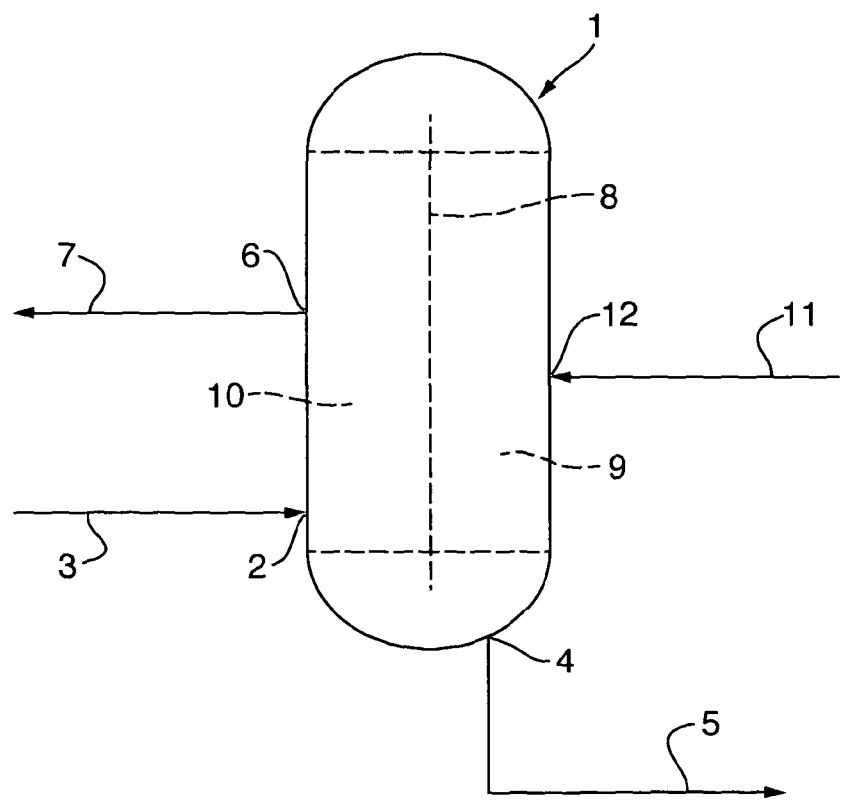

PROCESS AND SYSTEM FOR THE SEPARATION OF SOLID CARBOXYLIC ACID FINES

The present invention relates to a process for the recovery of solid carboxylic acid fines, preferably solid aromatic carboxylic acid fines, from mother liquor and a system therefore. More particularly, it relates to a process for the recovery of solid terephthalic acid fines from mother liquor and a system for said separation.

Typically crude terephthalic acid is produced by the oxidation of p-xylene. The oxidation is conducted using acetic acid as solvent in the presence of a catalyst. The solution is then cooled in a stepwise manner to crystallise the terephthalic acid. The terephthalic acid must then be separated from the mother liquor which is generally a combination of acetic acid, water, organics and oxidation catalyst. The terephthalic acid crystals are generally separated from the mother liquor by filtration. This separation may be carried out using a rotary vacuum filter. An example of a rotary vacuum filter is described in US2002/0003117. The mother liquor will then generally be recycled to the reactor.

Whilst the filter systems used will generally remove the majority of the crystals from the mother liquor, they are not 100% effective and therefore some solid crude terephthalic acid particles pass through the filter cloth and remain in the mother liquor. These solid particles are known as fines and will generally be smaller than the apertures in the filter cloth.

Due to the nature of the oxidation reaction for the production of terephthalic acid, numerous impurities are generated. Since the mother liquor is recycled, these impurities build up in the mother liquor and it is therefore necessary to take a purge from the mother liquor between the filtration step and the liquor being reintroduced to the reactor. Generally, the purge is pumped from the bottom of the drum which collects the mother liquor from the filter. However, since the mother liquor still contains terephthalic acid, taking the purge removes terephthalic acid from the system which represents a loss of product and therefore reduces the economics of the system.

Proposals have been made to recover the terephthalic acid from the purge stream in an attempt to improve the economics of the system. One proposal is discussed in EP 0882009 in which the mother liquor is split into a recycle fraction and a purge fraction. In the proposed process, the purge fraction is subjected to solid-liquid separation in a filtration unit to remove fines. The mother liquor is then concentrated in an evaporator before being returned to the reactor. The removal of the fines reduces the load on the evaporator and facilitates the recovery of greater amounts of the solvent along with recovery of the aromatic carboxylic acid fines which can be recycled to the reactor.

Whilst this arrangement mitigates the loss of terephthalic acid, the provision and operation of the additional apparatus increases the capital and operating costs of the process. However, since the operating costs are significant in comparison with the amount of terephthalic acid recovered, the proposal may not offer substantial cost benefits over the lifetime of the plant.

In copending UK application numbers 1008412.7, 1010856.1 and 1010857.9, it has been proposed that the separation of the carboxylic acid crystals, preferably aromatic carboxylic acid crystals, from the slurry in which they are formed can advantageously be carried out using a pressure filter, preferably a rotary pressure filter. Operating the filter at pressure will enable the mother liquor collection drum to be at pressure. This means that the purge does not have to be taken using a pump nor does it have to be removed from the bottom of the vessel. This will allow the drum to act as a gravity separation device in which the solid fines will sink to the bottom of the drum. As the purge can then be taken above the level of settled fines, it will not contain solids and these are therefore not lost to the system. The settled fines can subsequently be recovered.

Thus according to the present invention there is provided a process for the separation of solid carboxylic acid fines from mother liquor comprising said fines, wherein said process comprises the steps of:

feeding the mother liquor containing fines to a settlement drum at above atmospheric pressure; and removing mother liquor having a lower concentration of carboxylic fines than that fed to the settlement drum; wherein said mother liquor removal occurs at a point above the point at which the mother liquor containing fines is fed to the settlement drum.

According to a second aspect of the present invention there is provided a system for the separation of solid carboxylic acid fines from mother liquor, said system comprising:

a settlement drum having an inlet for mother liquor comprising carboxylic acid fines and an outlet for mother liquor having a lower concentration of carboxylic acid fines content then that of the mother liquor introduced via the inlet;

wherein said settlement drum is configured to operate at above atmospheric pressure and said outlet is located at a point in the settlement drum above said inlet.

In a preferred method and system, the carboxylic acid fines are aromatic carboxylic acid fines.

In a preferred method and system, the stream of mother liquor removed from the settlement drum via the outlet above the inlet for the mother liquor and fines will be substantially free of carboxylic acid fines.

The mother liquor removed from the point above the inlet may be the purge stream in which arrangement a second outlet may be provided to allow mother liquor to be removed to be returned to the reactor for the production of the carboxylic acid. In an alternative arrangement, the mother liquor removed from the point above the inlet is a stream which is separated after removal from the settlement drum with a portion being removed as purge and a portion recycled to the reactor. It will be appreciated that generally that only a portion of the mother liquor will be removed from the outlet and that the bulk will be returned with the fines to the reactor.

The process and system of the present invention are suitable for use with any crystalline carboxylic acid but is particularly suitable for the separation of aromatic carboxylic acid fines. In particular, they are suitable for us in the separation of crude terephthalic acid fines from mother liquor comprising acetic acid or the separation of pure terephthalic acid fines from mother liquor comprising water. By "pure terephthalic acid" we mean terephthalic acid which has been subjected to at least one purification process and as such is more pure than the crude terephthalic acid removed from the reactor in which it is formed. Further, the process and system are also particularly useful for the separation of crude isophthalic acid from the stream in which they are contained. "Crude" and "pure" in connection with the isophthalic acid have meanings corresponding to those described above in connection with terephthalic acid.

The settlement drum may be at any suitable pressure above ambient pressure.

The present invention enables the fines to be separated from the mother liquor efficiently without the need for apparatus which is expensive to install and operate. Since no additional equipment is required, any recovered product is a direct cost saving for the process.

In one arrangement the settlement drum may include one or more structures which facilitate settlement of the fines. Such structures are well known in the art. In one arrangement, the device may include tilted plates. The angle of the tilt of said plates may be adjustable such that the operation of the device may be optimised. The angle of the plates may be adjustable manually or automatically. The adjustment may preferably be carried out without the need to stop the process.

In the bulk process for removing the bulk carboxylic acid crystals in the filter it is conventional to wash the filter cake to remove items such as catalyst to prevent these from being lost to the system. The solvent used to wash the cake will generally be the same solvent as that in which the carboxylic acid crystals were slurried on their introduction to the filter. However, the wash solvent will not contain the impurities that build up from the oxidation reaction and is therefore regarded as clean. Generally this clean stream is kept separate from the mother liquor from the reactor which contains impurities and which is regarded as dirty.

Traditionally, it was important to keep these clean and dirty streams separate and thus after they passed through the filter they were sent to respective, separate, vessels. The purge is then taken from the dirty stream without taking any of the clean stream from the system. However, the requirement to have two separate vessels and associated piping, etc, adds to the capital and operating costs of the process.

However, in the present invention it is possible to provide the settlement drum with a baffle to effectively separate it into two sides; a dirty side and a clean side. Thus in a preferred arrangement, the settlement drum comprises a baffle. In this arrangement, the inlet of mother liquor and fines will be located on the dirty side and the outlet for mother liquor having reduced carboxylic acid fines content is also taken from the dirty side. Clean wash solvent can be fed, via a separate inlet, to the clean side of said settlement drum.

Whilst the mother liquor from the dirty side may overflow the baffle, in a preferred arrangement, an underflow will be provided as this will facilitate settlement of the fines. Mixing of the mother liquor from the dirty side with the wash solvent on the clean side will be minimal.

The present invention will now be described, by way of example, with reference to the accompanying drawing:

FIG. 1 is a schematic representation of a settlement drum of a preferred arrangement of the present invention.

It will be understood by those skilled in the art that the drawings are diagrammatic and that further items of equipment such as reflux drums, pumps, vacuum pumps, compressors, gas recycle compressors, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

By way of example, the process and system of the present invention will be described with reference to the separation of terephthalic acid fines from acetic acid.

The settlement drum 1 comprises an inlet 2 through which mother liquor comprising terephthalic fines from the pressure filter is added in line 3. The fines settle in the settlement drum and are removed via outlet 4 and returned to the oxidation reactor in line 5. A purge is removed from outlet 6 and passed in line 7 to a solvent stripper. The settlement drum includes a baffle 8 which effectively separates the drum into a clean side 9 and a dirty side 10. Clean solvent from the wash in the filter is supplied to the settlement drum via line 11 and inlet 12.

The invention will now be described with reference to the following non-limiting examples.

EXAMPLE 1

Mother liquor including terephthalic acid is supplied in line 3 to the settlement drum 1 of FIG. 1. It will be understood that the amount of solid settling which will occur is determined by the particle size distribution of the solids in the stream. Typically, the terephthalic acid solids distribution found in the mother liquor stream is that set out in Table 1.

TABLE 1

| | Particle size (µm) | | | |
|---|---|---|---|---|
| | <50 | 50-100 | 100-200 | >200 |
| % by mass | 10% | 30% | 40% | 20% |

There are several known methods for calculating settling velocity. One is the use o Stokes Law:

$$Uo = d^2 \cdot g \cdot (\rho S - \rho L)/(18 \cdot \mu)$$

where:
Uo=settling velocity (m/s)
d=particle size (m)
g=gravitational constant (9.81 m/s²)
ρS=density of solids (kg/m³)
ρL=density of liquid (kg/m³)
μliquid viscosity (Ns/m²)

(Reference: Coulson & Richardson, Chemical Engineering, Volume 2 (3$r^d$ Edition), page 94, Equation 3.19)

For a terephthalic acid particle of 50 micron diameter, the settling velocity in the mother liquor stream is approximately 1.5 mm/s.

In this example, the size of the settling drum 1 and position of the internal baffle 8 are set to achieve an upward velocity (Vo) of stream 7 within the settling drum of less than 1.5 mm/s.

Hence all particles of size greater than 50 microns will settle downwards and leave the drum via stream 5.

Based upon the above particle size distribution, the solids flowrate in stream 7 will be only 10% of the solids flow rate of stream 3.

The resulting compositions of the streams are detailed in Table 2.

TABLE 2

| | Stream Number | | | |
|---|---|---|---|---|
| | 3 | 11 | 7 | 5 |
| | Description | | | |
| Flow rates (kg/h) | Mother liquor from filter | Wash liquor from filter | Purge to solvent stripper | Recycle to Oxidation Reactor |
| Solids | 745 | 12 | 11 | 746 |
| Liquid | 148255 | 24721 | 22339 | 150637 |
| Total | 149000 | 24733 | 22350 | 151383 |
| Solids (% w/w) | 0.50 | 0.05 | 0.05 | 0.49 |

COMPARATIVE EXAMPLE 2

This example shows the effect of the prior art where the two streams (mother liquor and wash liquor) are simply combined in one vessel. An amount is purged from the process in order to remove dissolved impurities and any undissolved solids (comprising mostly terephthalic acid solids) are also lost from the process and this represents an inefficiency and incurs additional operating costs through increased paraxylene usage. The stream compositions for this arrangement are set out in Table 3. The stream numbers relate to the corresponding streams in Example 1.

TABLE 3

| Flow rates (kg/h) | Stream Number | | | |
|---|---|---|---|---|
| | 3 | 11 | 7 | 5 |
| | Description | | | |
| | Mother liquor from filter | Wash liquor from filter | Purge to solvent stripper | Recycle to Oxidation Reactor |
| Solids | 745 | 12 | 114 | 643 |
| Liquid | 148255 | 24721 | 25946 | 147030 |
| Total | 149000 | 24733 | 26060 | 147673 |
| Solids | 0.50 | 0.05 | 0.44 | 0.44 |

Typically 15% of stream 3 is purged from the process, but since streams 3 and 11 are mixed together, 15% of stream 11 is also purged unnecessarily.

Thus, Comparative Example 1 the amount of solids lost in purge stream is 114 kg/h and the solids concentration in streams 5 and 7 is the same as the vessel is fully mixed.

A comparison of Example 1 with Comparative Example 2, indicates that compared to Comparative Example 2, the loss of terephthalic solids in the purge (stream 7) of Example 1 has been reduced by more than 90%.

In addition the flow rate of stream 7 has been reduced by almost 15% which will result in additional capital cost savings in the downstream equipment used in the process in this purge stream.

The invention claimed is:

1. A process for the separation of solid carboxylic acid fines from mother liquor comprising said fines, wherein said process comprises the steps of:
   feeding the mother liquor containing fines to a settlement drum at above atmospheric pressure;
   removing a minor portion of the mother liquor, this portion having a lower concentration of carboxylic fines than that fed to the settlement drum; and
   removing the remainder of the mother liquor containing fines;
   wherein the removal of the portion of the mother liquor having a lower concentration of carboxylic fines than that fed to the settlement drum occurs at a point above the point at which the mother liquor containing fines is fed to the settlement drum.

2. The method of claim 1 wherein the carboxylic acid fines are aromatic carboxylic acid fines.

3. The method of claim 1 wherein the stream of mother liquor removed from the settlement drum at the outlet above the inlet for the mother liquor is free of carboxylic acid fines.

4. The method of claim 1 wherein the carboxylic acid fines are crystalline and are crude terephthalic acid fines or pure terephthalic acid fines.

5. The method of claim 1 wherein the carboxylic acid fines are crystalline and are crude isophthalic acid fines or pure isophthalic acid fines.

6. The method of claim 1 wherein the settlement drum includes one or more structures which facilitate settlement of the fines.

7. The method of claim 6 wherein the structure which facilitate settlement comprise tilted plates.

8. The method of claim 7 wherein the angle of the tilt of said plates is adjustable.

9. The method of claim 1 wherein the settlement drum includes a baffle to divide the drum into a dirty side and a clean side.

10. The method of claim 9 wherein washing solvent is supplied to the clean side of the drum via an inlet.

* * * * *